United States Patent
Ohishi

(10) Patent No.: US 10,390,786 B2
(45) Date of Patent: Aug. 27, 2019

(54) X-RAY DIAGNOSTIC APPARATUS

(71) Applicant: TOSHIBA MEDICAL SYSTEMS CORPORATION, Otawara-Shi (JP)

(72) Inventor: Satoru Ohishi, Otawara (JP)

(73) Assignee: Canon Medical Systems Corporation, Otawara-shi (JP)

(*) Notice: Subject to any disclaimer, the term of this patent is extended or adjusted under 35 U.S.C. 154(b) by 777 days.

(21) Appl. No.: 14/982,523

(22) Filed: Dec. 29, 2015

(65) Prior Publication Data

US 2016/0192894 A1 Jul. 7, 2016

(30) Foreign Application Priority Data

Jan. 5, 2015 (JP) ................................ 2015-000158

(51) Int. Cl.
*A61B 6/00* (2006.01)
*G06F 19/00* (2018.01)

(52) U.S. Cl.
CPC ............ *A61B 6/5294* (2013.01); *A61B 6/463* (2013.01); *A61B 6/504* (2013.01); *G06F 19/321* (2013.01)

(58) Field of Classification Search
CPC ....... A61B 6/463; A61B 6/504; A61B 6/5294; G06F 19/321; G06F 3/0482; G06F 3/04842
See application file for complete search history.

(56) References Cited

U.S. PATENT DOCUMENTS

| | | | | |
|---|---|---|---|---|
| 5,465,378 A | * | 11/1995 | Duensing | G06F 3/16 715/233 |
| 5,715,449 A | * | 2/1998 | Peters, Jr. | G06F 17/22 |
| 6,366,683 B1 | * | 4/2002 | Langlotz | G16H 15/00 382/128 |
| 8,195,594 B1 | * | 6/2012 | Bryce | G16H 15/00 706/47 |
| 8,401,259 B2 | * | 3/2013 | Matsue | G06F 19/321 382/128 |

(Continued)

FOREIGN PATENT DOCUMENTS

| | | |
|---|---|---|
| JP | 2008-259661 | 10/2008 |
| JP | 2009-515599 | 4/2009 |

(Continued)

OTHER PUBLICATIONS

Office Action dated Nov. 6, 2018 in Japanese Patent Application No. 2015-000158.

*Primary Examiner* — Andrea N Long
(74) *Attorney, Agent, or Firm* — Oblon, McClelland, Maier & Neustadt, L.L.P.

(57) ABSTRACT

In one embodiment, an X-ray diagnostic apparatus generating an object image by detecting X-rays having passed through an object includes: a display configured to display the object image; memory circuitry configured to store feature information items for distinguishing the object image from other images; processing circuitry configured to perform display-order change processing which is processing of changing display order of the feature information items, and to cause the display to display the feature information items subjected to the display-order change processing as alternates; and an input circuit configured to receive input of selecting a feature information item from the displayed feature information items.

20 Claims, 7 Drawing Sheets

(56) References Cited

U.S. PATENT DOCUMENTS

| | | | |
|---|---|---|---|
| 2003/0156745 A1* | 8/2003 | Saito | G06F 19/321 382/128 |
| 2004/0078215 A1* | 4/2004 | Dahlin | G06Q 10/10 705/2 |
| 2004/0242998 A1* | 12/2004 | Pan | A61B 8/467 600/437 |
| 2008/0052126 A1* | 2/2008 | Sasai | G06F 17/30265 705/3 |
| 2008/0109250 A1* | 5/2008 | Walker | G06F 17/2247 705/2 |
| 2010/0061608 A1* | 3/2010 | Galant | G06T 7/11 382/128 |
| 2011/0242096 A1* | 10/2011 | Kitamura | G06F 17/2765 345/419 |
| 2013/0028494 A1* | 1/2013 | Groth | G06T 7/0012 382/130 |
| 2015/0005630 A1* | 1/2015 | Jung | A61B 8/565 600/437 |
| 2015/0235008 A1* | 8/2015 | Sasai | G06F 19/3487 715/771 |
| 2017/0235903 A1* | 8/2017 | McLaughlin | G06F 19/00 715/708 |

FOREIGN PATENT DOCUMENTS

| | | |
|---|---|---|
| JP | 2012-249960 | 12/2012 |
| JP | 2014-512897 | 5/2014 |

* cited by examiner

| FEMORAL ARTERY | DESCENDING AORTA | AORTIC ARC |
|---|---|---|
| LEFT SUBCLAVIAN ARTERY | RIGHT SUBCLAVIAN ARTERY | BRACHIOCEPHALIC ARTERY |
| COMMON CAROTID ARTERY | RIGHT INTERNAL CAROTID ARTERY | RIGHT ANTERIOR CEREBRAL ARTERY |
| RIGHT MIDDLE CEREBRAL ARTERY | LEFT INTERNAL CAROTID ARTERY | LEFT ANTERIOR CEREBRAL ARTERY |
| LEFT MIDDLE CEREBRAL ARTERY | LEFT VERTEBRAL ARTERY | RIGHT VERTEBRAL ARTERY |
| BASILAR ARTERY | RIGHT EXTERNAL CAROTID ARTERY | LEFT EXTERNAL CAROTID ARTERY |
| OBSERVATIONAL ANGLE | CONTRAST AGENT | ANTIPLATELET AGENT |
| ANTICOAGULANT AGENT | THROMBOLYTIC | GUIDEWIRE |
| CATHETER | STENT FOR CAROTID ARTERY | INTRACRANIAL STENT |
| BALLOON | PREPARATORY EXPANSION | EX-POST EXPANSION |
| COIL EMBOLIZATION | STENT PLACEMENT | FIRST COIL |
| SECOND COIL | THIRD COIL | DOME FILLING COIL |
| CATHETER INSERTION | STENT-ASSISTED COIL EMBOLIZATION | DOUBLE CATHETER TECHNIQUE |
|  |  | BALLOON-ASSISTED COIL EMBOLIZATION |

FIG. 4

X-RAY DIAGNOSTIC APPARATUS

CROSS-REFERENCE TO RELATED APPLICATION

This application is based upon and claims the benefit of priority from Japanese Patent Application No. 2015-000158, filed on Jan. 5, 2015, the entire contents of which are incorporated herein by reference.

FIELD

Embodiments described herein relate generally to an X-ray diagnostic apparatus.

BACKGROUND

In an X-ray diagnostic apparatus, X-rays having passed through an object are detected by multiple detection elements arrayed in a matrix as an example, and an X-ray image in which each pixel shows luminance based on X-ray dosage of the corresponding detection element is generated.

In an X-ray diagnostic apparatus, information such as imaging conditions, name of a contrast-enhanced blood vessel, a performed medical procedure, and imaging conditions including an X-ray irradiation direction (i.e., an irradiation angle) for understanding various clinical situations can be inputted in a comment region of an X-ray DICOM data or the like.

Additionally, the above-described comment information is recorded on diagnosed images in some cases. As to input of information such as imaging conditions, a name of a contrast-enhanced blood vessel, and a performed medical procedure, there are two methods. In one of the two methods, a user selects the information to be inputted from plural choices. In the other of the two methods, a user manually enters a comment.

However, if the number of choices is too few in the method in which a user selects the information to be inputted from plural choices, an appropriate choice is not included in some cases. Additionally, if the number of choices is too many in the method in which a user selects the information to be inputted from plural choices, it takes longer for a user to select an appropriate choice from too many choices. Furthermore, in the method in which a user manually enters a comment, an operation of manually entering a comment is time-consuming for a user.

BRIEF DESCRIPTION OF THE DRAWINGS

FIG. 4 is a schematic diagram showing an example of every choice having been already stored in memory circuitry since the start-up time of the X-ray diagnostic apparatus out of all the comment alternates relevant to head imaging, when head imaging is designated in a treatment plan;

DETAILED DESCRIPTION

Figure 1:
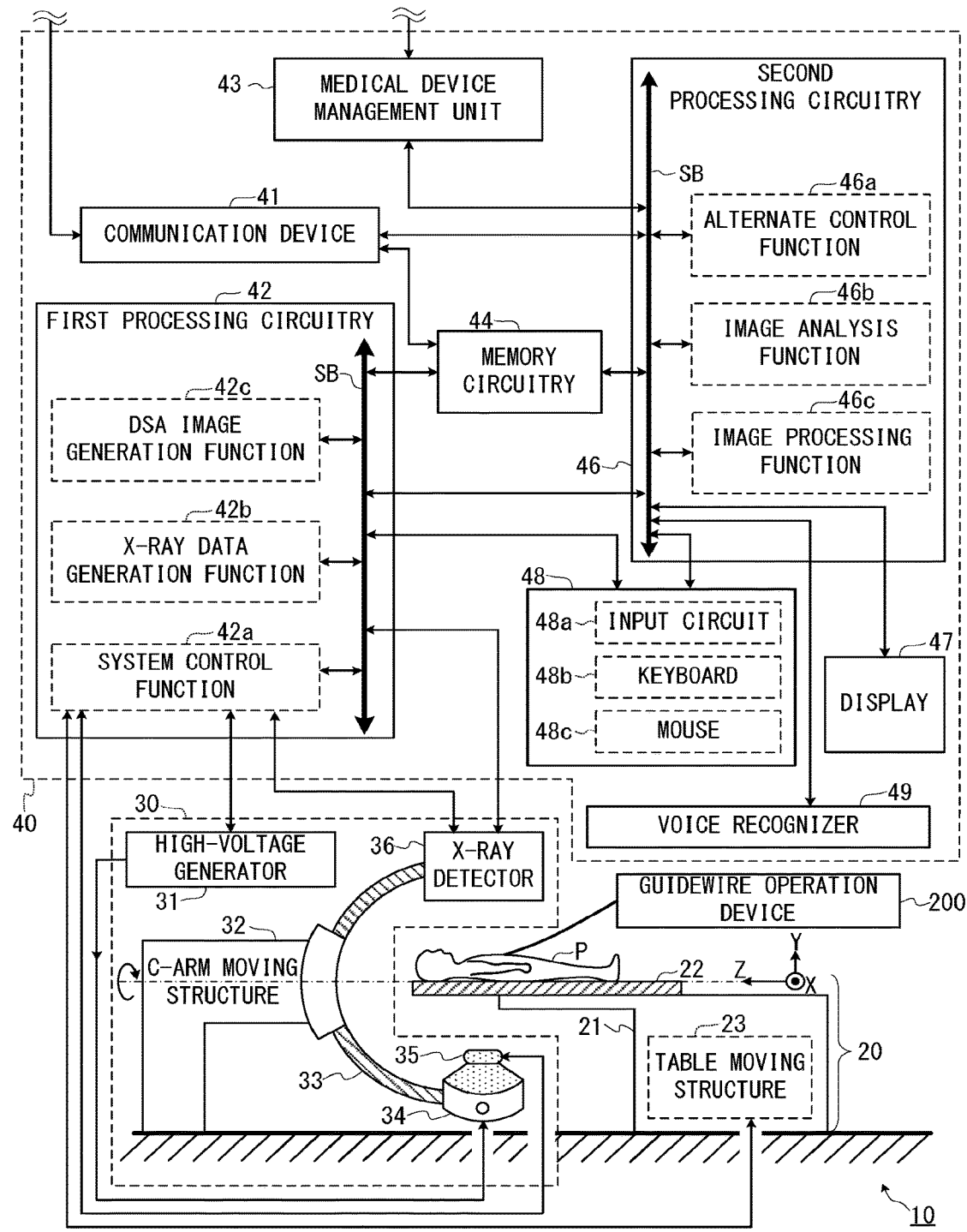
FIG. 1 is a block diagram showing an example of hardware configuration of an X-ray diagnostic apparatus of the present embodiment.

In one embodiment, an X-ray diagnostic apparatus which generates an object image by detecting X-rays having passed through an object includes: a display configured to display the object image; memory circuitry configured to store feature information items for distinguishing the object image from other object images; processing circuitry configured to perform display-order change processing which is processing of changing display order of the feature information items, and to cause the display to display the feature information items subjected to the display-order change processing as alternates; and an input circuit configured to receive input of selecting a feature information item from the feature information items displayed on the display.

Hereinafter, viewpoints of the inventor and a concept considered by the inventor will be explained first, and then concrete embodiments will be explained.

In an X-ray diagnostic apparatus, respective thumbnail images of a large number of generated X-ray images are collectively displayed and there is a case where one of the generated X-ray images is selected by designating the thumbnail image corresponding to the X-ray image to be selected. In such a case, it is preferred to add feature information (i.e., representative information) for distinguishing each X-ray image from other X-ray images to each of the thumbnail images with a comment. The purpose of this work is to make it easy to select the image including information that the operator wants to check the image again after this work. In other words, this is not work of superimposing a comment on a partial region of an image as characters with predetermined luminance or color but work of adding a comment to accompanying information of an image file.

Moreover, an operator sometimes leaves a record indicative of contents of diagnosis or medical treatment performed by doctors. In this case, a doctor selects an objective time-sequential X-ray image or DSA image from a large number of time-sequential X-ray images or DSA images based on previous feature information or the like(e.g., a name of cured blood vessel and a phase of treatment), and then selects a representative X-ray image or DSA image from time-sequential X-ray image or DSA image as diagnosis or treatment record with a comment. This comment has a meaning of making it easy to recognize for what purpose and under what conditions this image is generated. This comment is added to an image region of the corresponding X-ray image as textual information in such a manner that a target region of this image is avoided (e.g., if the upper left region of this image is the target region, characters are superimposed on the lower right region of the image being opposite to the target region).

Either of the above-described two types of work is an operational burden for a user, if a user enters a comment as character data with a keyboard. For the above reason, as an idea of reducing an operational burden, an X-ray diagnostic apparatus side may automatically display choices so that a user can select one of the displayed choices as a comment for the X-ray image. In this case, plural choices automatically displayed by the X-ray diagnostic apparatus side may be selected from, for example, information items related to at least one of examination and treatment such as an X-ray irradiation direction, a name of a blood vessel projected on an image, and a name of medical agent used for contrast agent.

Incidentally, the above-described "information items related to at least one of examination and treatment" means, for example, information relevant to at least one of examination and treatment performed during imaging of the X-ray image such as patient information, contents of the examination, and contents of the treatment. Hereinafter, the above-described information items related to at least one of examination and treatment are referred to as information items on examination and/or treatment.

However, if the number of choices automatically displayed by an X-ray diagnostic apparatus side is one hundred or more as an example, a user has to scroll down the choices to check all the choices including the bottommost choice. In this case, it is considered that a user needs more time for selecting a comment. On the other hand, if the number of choices automatically displayed by an X-ray diagnostic apparatus side is less than five as an example, the number of choices is too few and a case where a choice reflecting feature information making the X-ray image distinguishable from other X-ray images is not included in the displayed choices may occur.

For the above reason, in order to reduce an operational burden for a user in the above-described work of adding a comment, alternates for feature information items to be used for a comment of an X-ray image are narrowed down to appropriate number by performing extraction processing based on the information items on examination and/or treatment of the target X-ray image in the embodiments described below. Although an example in which the appropriate number of comment alternates is approximately ten to twenty will be explained in the embodiments described below, this is only an example for concretizing the explanation and making it easy to understand. The appropriate number of comment alternates is not limited to approximately ten to twenty, and it may be approximately fifteen to thirty as an example.

Hereinafter, embodiments of the present invention will be explained with reference to the accompanying drawings. Note that the same reference numbers are given for identical components in each figure, and duplicate explanation is omitted.

<Configuration of Present Embodiment>

FIG. 1 is a block diagram showing an example of hardware configuration of the X-ray diagnostic apparatus 10 of the present embodiment. As an example here, components of the X-ray diagnostic apparatus 10 will be explained by classifying them into three groups: a bed device 20, an X-ray generation/detection system 30, and a computing system 40.

Firstly, the bed device 20 includes a supporting platform 21, a table 22, and a table moving structure 23 disposed inside the supporting platform 21. An object P is loaded on the table 22. Depending on contents of medical treatment, at least one of a guidewire operation device 200 and a non-illustrated contrast agent injection apparatus is inserted into the object P loaded on the table 22.

The supporting platform 21 supports the table 22 in such a manner that the table 22 can move in the horizontal direction (i.e., along an X-Z plane of the apparatus coordinate system). The table moving structure 23 positions an imaging region of the object P between an X-ray detector 36 and a collimator 35 described below, by moving the table 22 along an X-Z plane of the apparatus coordinate system under control of a system control function 42a of the computing system 40 described below.

As an example here, the above-described apparatus coordinate system whose X axis, Y axis and Z axis are perpendicular to each other is defined as follows.

First, the Y axis direction is defined as the vertical direction, and the table 22 is disposed at such a position that the direction of the normal line of its top surface becomes equal to the Y axis direction. The horizontal moving direction of the table 22 is defined as the Z axis direction, and the table 22 is disposed in such a manner that its longitudinal direction becomes equal to the Z axis direction. The X axis direction is the direction perpendicular to these Y axis direction and Z axis direction.

Secondly, the X-ray generation/detection system 30 includes a high-voltage generator 31, a C-arm moving structure 32, a C-arm 33, an X-ray tube 34, the collimator 35, and the X-ray detector 36.

The C-arm 33 is an arm which supports the X-ray tube 34, the collimator 35, and the X-ray detector 36. The X-ray detector 36 and the pair of the X-ray tube 34 and the collimator 35 are arranged by the C-arm 33 so as to face each other with the object P interposed therebetween.

The C-arm moving structure 32 rotates and moves the C-arm 33 according to an imaging region, under control of the system control function 42a.

The high-voltage generator 31 generates high voltage and supplies the X-ray tube 34 with the generated high voltage.

The X-ray tube 34 generates X-rays by using the high voltage supplied from the high-voltage generator 31.

The collimator 35 narrows down an irradiation range of X-rays by, for example, sliding collimation blades so that an imaging region of the object P is selectively irradiated with X-rays, and controls the irradiation range by adjusting degree of opening of the collimation blades.

The X-ray detector 36 includes, for example, a large number of non-illustrated X-ray detection elements arrayed in a matrix for converting X-rays into electric signals. The X-ray detector 36 converts X-rays having passed through the object P into electric signals to accumulate these electric signals by using these X-ray detection elements, and outputs the accumulated electric signals to an X-ray data generation function 42b of the computing system 40 described below.

Thirdly, the computing system 40 includes a communication device 41, first processing circuitry 42, a medical device management unit 43, memory circuitry 44, second processing circuitry 46, a display 47, an input device 48, and a voice recognizer 49.

Out of these components of the computing system 40, the second processing circuitry 46, the display 47, the input device 48, and the voice recognizer 49 functions as a support system for inputting image feature information items (i.e., a comment input support device) as a whole.

The communication device 41 is connected to, for example, an in-hospital network such as a PACS (Picture Archiving and Communication System). The communication device 41 acquires volume data from, for example, an X-ray CT (Computed Tomography) apparatus via the in-hospital network and stores the acquired volume data in the memory circuitry 44.

Incidentally, "image data" includes image data of a three-dimensional image and image data of a two-dimensional image in a broad sense. For distinction in the present specification, image data of a two-dimensional image are referred to as image data, and image data of a three-dimensional image are referred to as volume data.

In addition, the above-described "projection" means, for example, to project a three-dimensional object on a two-dimensional image, and the above-described projection data means data of a two-dimensional image obtained by projecting a three-dimensional object.

The first processing circuitry 42 controls an imaging operation of the X-ray diagnostic apparatus 10. The first processing circuitry 42 includes the system control function 42a, an X-ray data generation function 42b, a DSA (Digital Subtraction Angiography) image generation function 42c, and a system bus SB as communication wiring interconnecting these components.

The first processing circuitry 42 is a processor configured to implement functions corresponding to respective programs by reading out the programs from a memory (i.e., the memory circuitry 44) and executing the programs. In other words, the first processing circuitry 42 (processor) implements the system control function 42a, the X-ray data generation function 42b, and the DSA image generation function 42c by reading out the respective programs.

Here, the system control function 42a is a function of controlling the entirety of the X-ray diagnostic apparatus 10 in setting of imaging conditions, an imaging operation, and display processing.

The X-ray data generation function 42b is a function of generating projection data of X-ray images by using electrical signals converted from X-rays having passed through the object P by the X-ray detector 36 and storing the generated projection data in the memory circuitry 44. As an example here, an X-ray image is assumed to be an image which is obtained by determining luminance of each pixel based on an electrical signal outputted from each of X-ray detection elements of the X-ray detector 36 and is not subjected to image processing with the use of another image or data.

The DSA image generation function 42c is a function of (a) acquiring projection data of an X-ray image (mask image) obtained before injecting contrast agent and projection data of X-ray images of respective time phases obtained after injecting contrast agent and (b) generating image data of DSA images corresponding to the respective time phases by calculating subtraction between the mask image and each of X-ray images obtained after injecting contrast agent. The DSA image generation function 42c stores the image data of DSA image in the memory circuitry 44.

In the present specification, the term "object image" is used for meaning both of an X-ray image and an image derivatively generated from one or plural X-ray images. An image derivatively generated from one or plural X-ray images means, for example, the above-described DSA image and the like.

The medical device management unit 43 stores information on past use of respective medical devices used for examination and treatment to the object P together with the X-ray diagnostic apparatus 10, and updates and stores current usage conditions of the respective medical devices on a real-time basis. The above-described medical device means, for example, a guidewire, a catheter, a stent, a balloon, an embolic coil, and the like.

As to configuration of identifying a medical device aside from the medical device management unit 43, a signal generation unit may be provided on a non-illustrated operation unit of a medical device. This is so that the X-ray diagnostic apparatus 10 can acquire information relevant to identification of each medical device such as a currently-used medical device and operation history of a medical device based on a medical device information signal transmitted from the signal generation unit. Additionally or alternatively, as to identification of a medical device, a user may select the medical device to be identified from plural choices.

The second processing circuitry 46 determines alternates for a feature information item used for a comment of an object image, and causes the display 47 to display the determined alternates. In addition, the second processing circuitry 46 performs window conversion on image data or volume data of an object image, and causes the display 47 to display the object image subjected to the window conversion.

The above-described window conversion means conversion processing on a target image in which gradation expression of each pixel exceed a predetermined bit number. To be concrete, in window conversion, the window center (i.e., window level) and window width with respect to a target image are determined and thereby gradation of each pixel of the target image is rounded to gradation which can linearly displayed by the display 47.

The second processing circuitry 46 includes a alternate control function 46a, an image analysis function 46b, an image processing function 46c, and a system bus SB as communication wiring interconnecting these components.

The second processing circuitry 46 is a processor configured to implement functions corresponding to respective programs by reading out the programs from a memory (e.g., the memory circuitry 44) and executing the programs. In other words, the second processing circuitry 46 (processor) can implement the alternate control function 46a, the image analysis function 46b, and the image processing function 46c by reading out the respective programs.

Here, the alternate control function 46a is a function of performing extraction processing so as to determine appropriate number of alternates for a feature information item used as a comment of an object image. Hereinafter, the appropriate number of alternates for a feature information item used as a comment of an object image are referred to as comment alternates. The extraction processing includes processing of selecting comment alternates whose number is the appropriate number or less from many alternates and processing of generating comment alternates without selecting any alternate manually.

In other words, extraction processing includes, for example, (a) selection of comment alternates from information items on examination and/or treatment during imaging included in accompanying information of a file of an object image, (b) selection of comment alternates from plural blood vessel names identified by the image analysis function 46b, and (c) processing of generating a comment alternates by text data converted from voice by the voice recognizer 49 during examination or treatment. Details of the extraction processing will be described below.

In addition, the alternate control function 46a may change display order of comment alternates by performing display-order change processing. In this case, the second processing circuitry 46 causes the display 47 to display the plural comment alternates whose display order is changed by the display-order change processing. For example, the second processing circuitry 46 changes display order of plural comment alternates based on predetermined priority.

The image analysis function 46b includes a function of acquiring volume data generated by another image diagnostic apparatus with respect to the same object P after injection of contrast agent and storing the acquired data. The above-described same object P means an object being identical to the object depicted in one or plural object images for which comment alternates are extracted. The image analysis function 46b also includes functions of extracting a contour of each of blood vessels in the acquired volume data and identifying the name of each of the extracted blood vessels based on pattern matching between the contour of each of the extracted blood vessels and the contour stored as data for each blood vessel name.

The image processing function 46c is a function of performing image processing such as the above-described window conversion.

The display 47 displays an object image, a screen for setting imaging conditions, and plural alternates for a feature information item used as a comment of an object image, under the control of the second processing circuitry 46.

The input device 48 is configured of components such as an input circuit 48a, a keyboard 48b, and a mouse 48c. The input circuit 48a acquires various types of information and commands such as imaging conditions and a comment of an object image from the keyboard 48b, the mouse 48c, or a non-illustrated operation button for a user to input or select them. The input circuit 48a transfers the contents (e.g. various types of information and commands) inputted/selected by a user via the keyboard 48b, the mouse 48c, an operation button, or the like to the system control function 42a and the second processing circuitry 46.

The voice recognizer 49 detects voice around the object P in an examination or treatment period, converts the detected voice into text data, and stores the text data.

Hereinafter, processing of extracting comment alternates will be explained. In the case of an X-ray image obtained after injection of contrast agent (hereinafter, referred to as a contrast image) and an object image derivatively generated from one or plural contrast images, a name of a blood vessel is assumed to be included in comment alternates as an example here. As the first example of the processing of extracting comment alternates, an example of processing of extracting a name of a blood vessel will be explained.

Figure 2:
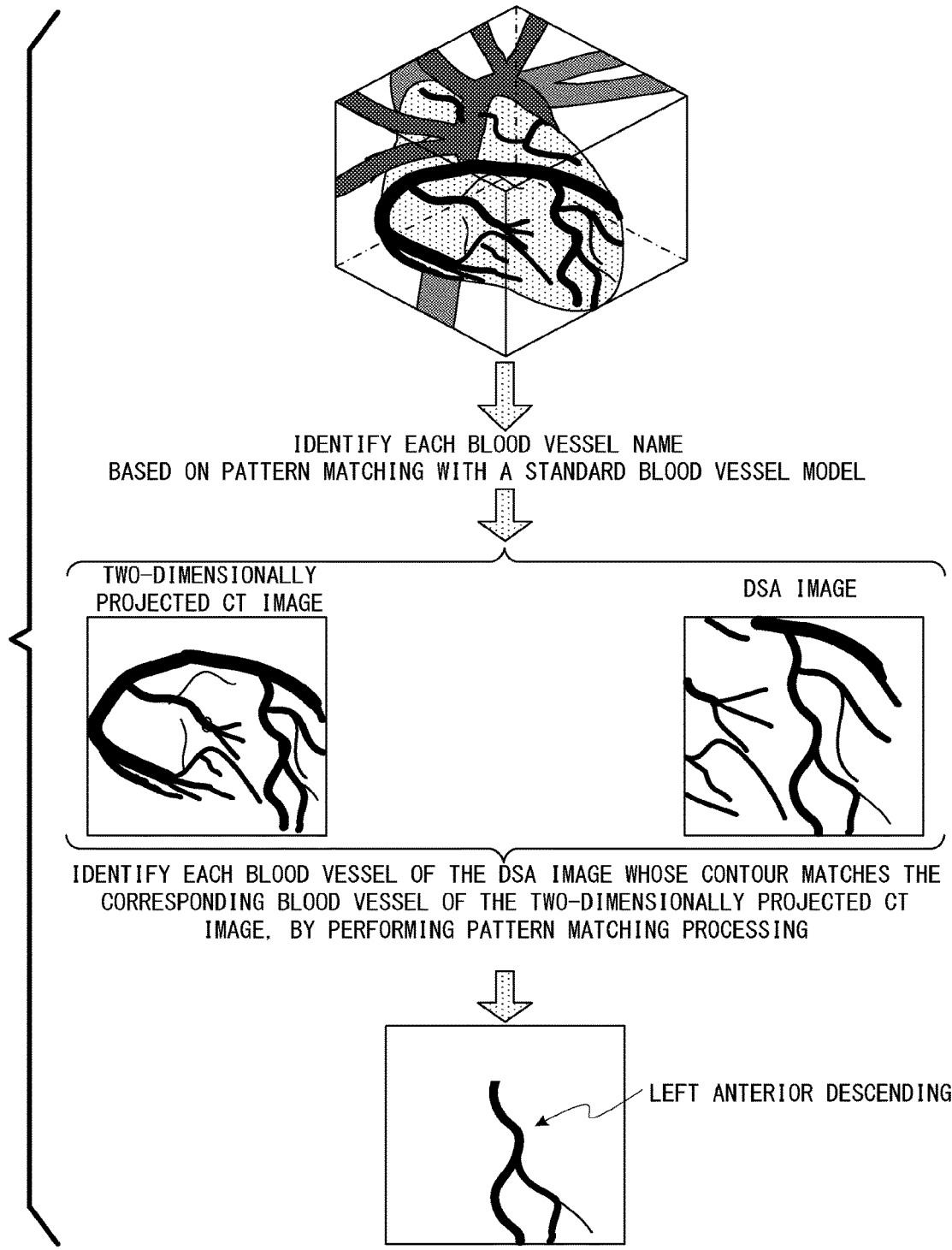
FIG. 2 is a schematic diagram showing an example of a method of identifying a name of a blood vessel in an object image by comparing the object image with volume data generated by another image diagnostic apparatus.

FIG. 2 is a schematic diagram showing an example of a method of identifying a name of a blood vessel in an object image by comparing the object image with volume data generated by another image diagnostic apparatus. Although a case where volume data generated by an X-ray CT apparatus after injection of contrast agent are used will be explained as an example here, volume data of a bloodstream image generated by another image diagnostic apparatus may be used. In the case of a magnetic resonance imaging apparatus as another example, though volume data imaged after injection of contrast agent may be used, volume data of a bloodstream image generated by a non-contrast electrocardiographic synchronization imaging under an ASL (Arterial Spin Labeling) technique may also be used.

The top part of FIG. 2 is a schematic oblique diagram showing an example of a three-dimensional image indicated by volume data around a heart generated by an X-ray CT apparatus. The image analysis function 46b extracts contours of blood vessels from the above-described volume data by performing known blood-vessel extraction processing in which threshold processing on luminance level for each voxel (i.e., pixel having depth) is included.

Here, data of a standard blood vessel model of a human body are preliminarily stored in the memory circuitry 44. The above-described data of a standard blood vessel model mean, for example, data of names of respective blood vessels and their standard contours (shapes). In addition, the above-described "preliminarily" means, for example, before an imaging operation by the X-ray diagnostic apparatus 10. Thus, the standard blood vessel model of a human body may be stored as data at the time of installation and adjustment work of the X-ray diagnostic apparatus 10 or may be regularly updated to new data each time an inspection for maintenance of the X-ray diagnostic apparatus 10 is performed.

The image analysis function 46b identifies names of the respective blood vessels extracted from the volume data based on pattern matching processing between contours of the respective blood vessels extracted from the volume data and data of the standard blood vessel model being read from the memory circuitry 44.

Next, the image analysis function 46b acquires information on an X-ray irradiation direction and posture of the object P on the table 22 at the time of imaging from the accompanying information of the object image generated by the X-ray diagnostic apparatus 10. Thereby, the image analysis function 46b determines from which direction in the patient coordinate system the object image is imaged, based on the acquired information.

The patient coordinate system is, for example, defined as follows. That is, the horizontal direction (i.e., left-right direction) of the object P is defined as its X axis direction, and the front-to-rear direction of the object P is defined as its Y axis direction on the premise that the abdominal side is the front and the back side is the rear. Further, the topside-to-downside direction of the object P is defined as its Z axis direction on the premise that the head side is topside and foot side is downside along the direction of a straight-line approximation of the backbone.

For simplifying the explanation here, the object P is loaded on the table 22 in such a manner that the direction of straight-line approximation of the backbone becomes equal to the longitudinal direction of the table 22. In other words, it is assumed that each of the X axis, the Y axis, and the Z axis matches between the apparatus coordinate system and the patient coordinate system.

Next, the image analysis function 46b generates projection data of a two-dimensional image from the above-described volume data in such a manner that the projection direction of the two-dimensional image to be generated matches the projection direction of the object image generated by the X-ray diagnostic apparatus 10. In the middle part of FIG. 2, the image on the left side is a schematic diagram of a CT image two-dimensionally projected in the above manner and the image on the right side is a schematic diagram of the object image generated by the X-ray diagnostic apparatus 10.

Next, the image analysis function 46b extracts each blood vessel whose contour matches between the two-dimensionally projected CT image and the object image generated by the X-ray diagnostic apparatus 10, by performing pattern matching processing. The bottom part of FIG. 2 is a schematic diagram of an image in which only blood vessels of the object image determined to match blood vessels of the CT image by the pattern matching processing are emphasized (i.e., selectively depicted).

The image analysis function 46b has already recognized the name of each blood vessel of the object image determined to match the CT image, by the above-described image analysis including pattern matching processing on volume data. Accordingly, the image analysis function 46b identifies the name of each blood vessel in object image whose contour matches the corresponding blood vessel in the two-dimensionally projected CT image, and outputs the identified name of each blood vessel to the alternate control function 46a.

Here, the number of blood vessels (i.e., names of blood vessels) increases due to branch, as a blood vessel goes down to its peripheral side. In the case of the right side of the head as an example, a common carotid artery branches into a right internal carotid artery and a right external carotid artery at its downstream side. The right internal carotid artery branches into a right middle cerebral artery and a right anterior cerebral artery at its downstream side.

For the above reason, the alternate control function 46a determines whether a blood vessel on the downstream side of the blood vessel whose name is inputted from the image analysis function 46b exists or not, by referring to the data of a standard blood vessel model of a human body stored in the memory circuitry 44. If it exists, the alternate control function 46a determines the name of the blood vessel inputted from the image analysis function 46b and the name of each blood vessel on its downstream side as comment alternates, as an example here. Note that the number of the blood vessels on the downstream side to be included in comment alternates may be one or plural.

In addition, the alternate control function 46a can change comment alternates as to each blood vessel name identified by the image analysis function 46b. For example, the alternate control function 46a may change display order of comment alternates based on priority of a name of each blood vessel depicted in an object image. Incidentally, priority of each blood vessel name may be assigned to each blood vessel name in the standard blood vessel model of a human body and preliminarily stored in the memory circuitry 44.

Next, the second example of processing of extracting comment alternates will be explained. When a medical device used during imaging exists, the alternate control function 46a includes the name of this medical device in comment alternates. The X-ray diagnostic apparatus 10 can be used not only for simple generation of X-ray images as examination but also for medical treatment such as stent placement under fluoroscopic imaging (i.e., it also functions as an interventional X-ray diagnostic apparatus). Accordingly, when a medical device such as a stent was used during imaging as an example, time and date of use is recorded in the medical device management unit 43.

The alternate control function 46a acquires imaging time (including date) from the accompanying information of the file of the object image, acquires the name of the medical device used with the X-ray diagnostic apparatus 10 at the acquired imaging time from the medical device management unit 43. Then, the alternate control function 46a determines at least one of the acquired name of the medical device and a distinguishing name of a medical procedure relevant to this medical device as a comment alternate.

For example, when the medical device is a coil used for embolization of an arterial aneurysm and this coil is the first coil inserted in the medical procedure, the alternate control function 46a includes "first coil" as a comment in comment alternates. Similarly, when the medical device is a coil used for embolization of an arterial aneurysm and this coil is the second inserted in the medical procedure, the alternate control function 46a includes "second coil" in comment alternates.

Additionally or alternatively, when the medical device is a stent for stenosis treatment and the target blood vessel is in a cervical region, the alternate control function 46a determines at least one of "CAS (Carotid Artery Stenting)" and "stent" as a comment alternate.

Next, as the third example of the processing of extracting comment alternates, a method of determining a treatment stage at the time of imaging an object will be explained. As to an object image, the treatment stage at the imaging time of this object image is assumed to be included in comment alternates as an example here.

In general, the main procedure for advancing treatment is fixed for each treatment content. In the case of stent insertion as an example, (a) inserting a catheter to a lesion region as the first stage, (b) preparatory balloon expansion (i.e., dilate the blood vessel in the lesion region) as the second stage, (c) stent placement as the third stage, (d) ex-post balloon expansion as the fourth stage, and (e) contrast-enhanced imaging for confirmation (i.e., confirming that the operative treatment has been successfully completed) as the fifth stage may be included.

However, information on treatment stages is not included in accompanying information of a file of an object image in many cases. For the above reason, the alternate control function 46a can estimate a treatment stage by using the following information, for example.

Firstly, a name of a medical device acquired from the medical device management unit 43 can be used.

Secondly, both imaging times of the first and final frames of all the object images generated for the treatment, and the imaging time of the X-ray image which is the target for determining comment alternates can be used. The alternate control function 46a calculates time interval between the imaging time of the first frame and the imaging time of the final frame as a treatment period.

When the imaging time of the target X-ray image is in the beginning side of the treatment period in the treatment of stent insertion, the alternate control function 46a can eliminate ex-post balloon expansion as the fourth stage and contrast-enhanced imaging for confirmation as the fifth stage from alternates for the treatment stage.

When the imaging time of the target X-ray image is in the ending side of the treatment period in the treatment of stent insertion, the alternate control function 46a can eliminate insertion of a catheter to a lesion region as the first stage and preparatory balloon expansion as the second stage from alternates for the treatment stage.

The alternate control function 46a can estimate the treatment stage by selecting one of the treatment stages which remain as alternates by the above elimination method so that the medical device used at the imaging time of this X-ray image matches the content of the treatment stage to be selected.

Additionally, the alternate control function 46a can search words being recognized and converted into text data by the voice recognizer 49 during the treatment period for a keyword which was recognized slightly before the imaging time of this X-ray image and suggests the treatment stage. When there is a keyword (including a key phrase) suggesting the treatment stage such as "ex-post balloon expansion from now", the alternate control function 46a can determine the treatment stage suggested by this key phrase as a comment alternate.

Incidentally, the present embodiment is not limited to an example in which the alternate control function 46a specifies the treatment stage at the time of imaging the target image by selecting one of plural treatment stages included in the preliminarily determined procedure of advancing the treatment and determines the specified treatment stage as a comment alternate. Even if possible treatment stages are not preliminarily designated, the alternate control function 46a can specify the treatment stage at the time of imaging the target image and determine the specified treatment stage as a comment alternate.

Specifically, the main procedure of advancing the treatment is sometimes fixed in the case of using one of specific medical device like a coil for embolization of an arterial aneurysm as an example. Thus, the alternate control function 46a can determine which of the treatment stages included in the procedure of advancing the treatment determined from the name of the medical device acquired from the medical device management unit 43 corresponds to the target image. The alternate control function 46a can perform the above determination based on words which were converted into text data by the voice recognizer 49 as an example.

Additionally, the alternate control function 46a can determine a treatment stage as a comment alternate not only when setting as to progression of treatment stages is automatically performed by the X-ray diagnostic apparatus 10 but also when shift in setting of respective components of the X-ray diagnostic apparatus 10 in association with progression of treatment stages is manually performed.

For example, consider a case where respective components of the X-ray diagnostic apparatus 10 shift to setting suitable for the next treatment stage (e.g., preparatory balloon expansion) when a catheter reaches a lesion region and a doctor pushes a button of the input device 48 of the X-ray diagnostic apparatus 10. Even in such a case, the alternate control function 46a can determine the treatment stage at the imaging time of the target X-ray image as a comment alternate.

In addition, the alternate control function 46a may assign priority to each medical device name and each treatment stage, when the alternate control function 46a determines a name of a medical device or a treatment stage as a comment alternate. For example, the alternate control function 46a can assign higher priority to specific phrases such as ex-post balloon expansion and contrast-enhanced imaging for confirmation in stent insertion so that these phrases having higher priority are preferentially determined as comment alternates.

Moreover, in the case of coil embolization for an arterial aneurysm, the alternate control function 46a may determine VER (Volume Embolization Ratio) indicative of ratio of an occupied volume of a coil to a volume of an arterial aneurysm expressed in percentage as a comment alternate.

Specifically, the alternate control function 46a may acquire a volume of an arterial aneurysm from a measurement result based on a three-dimensional image or from a measurement result performed by another image diagnostic apparatus such as a magnetic resonance imaging apparatus and an X-ray CT apparatus. In addition, the alternate control function 46a may acquire an occupied volume of a coil from the medical device management unit 43.

Moreover, the X-ray diagnostic apparatus 10 may preliminarily store detailed information on medical devices including an occupied volume of a coil, or the alternate control function 46a of the X-ray diagnostic apparatus 10 may acquire necessary data from a dedicated database in which volumes of respective coils are collectively recorded. At this time, it is preferable that the alternate control function 46a attaches VER and information capable of uniquely identifying a coil to the image. As examples of the information capable of uniquely identifying a coil, a name, a diameter, and a length are included.

Consider a case of coil embolization for an arterial aneurysm where (a) ten coils are inserted, (b) to what extent blood flow toward the arterial aneurysm is interrupted is checked by generating DSA images each time of inserting one coil, and (c) these DSA images are included in a file of a treatment report, as an example. In this case, it is useful if the above-described VER is displayed. As an example in the present embodiment, at least one of the following two types of processing is performed in addition to display of VER when a coil is used.

The first processing is processing in which VER and information on each inserted coil (e.g., its name, its diameter, and its length) are added to the DSA image by the alternate control function 46a or the input device 48 when information on VER is obtained. In the first processing, to add means to superimpose coil information on a partial region of the DSA image as characters having fixed luminance or color, for example. Note that this partial region for superimposing coil information is selected by avoiding the target region. Thereby, a reader can understand insertion history of coils only by observing an image on a file of a treatment report, without referring to other data for the insertion history of coils after closing the file.

The second processing is processing in which information on each inserted coil (e.g., its name, its diameter, and its length) is added to the DSA image by the alternate control function 46a or the input device 48 when a coil is inserted but information on VER is not obtained. Also in this case, a reader can understand insertion history of coils only by observing an image on a file of a treatment report, without referring to other data for the insertion history of coils after closing the file.

As to information on each inserted coil, it may be added as a comment to a region outside the image in the image file, without adding character information to a part of the image like the above-described first or second processing.

In conventional technology, information entered or selected by a user's operation matches information added to an image file. On the other hand, as an example in the present embodiment, the X-ray diagnostic apparatus 10 may be configured to display generic terms as comment alternates and to add information concretizing the selected generic term to an image file when one of generic terms is selected for the image file by a user. Details of such configuration will be explained in the step S6 of FIG. 7 as a flowchart described below.

Next, as to an X-ray irradiation direction, what angle is likely to become feature information will be considered as the fourth example of the processing of extracting comment alternates.

Figure 3:
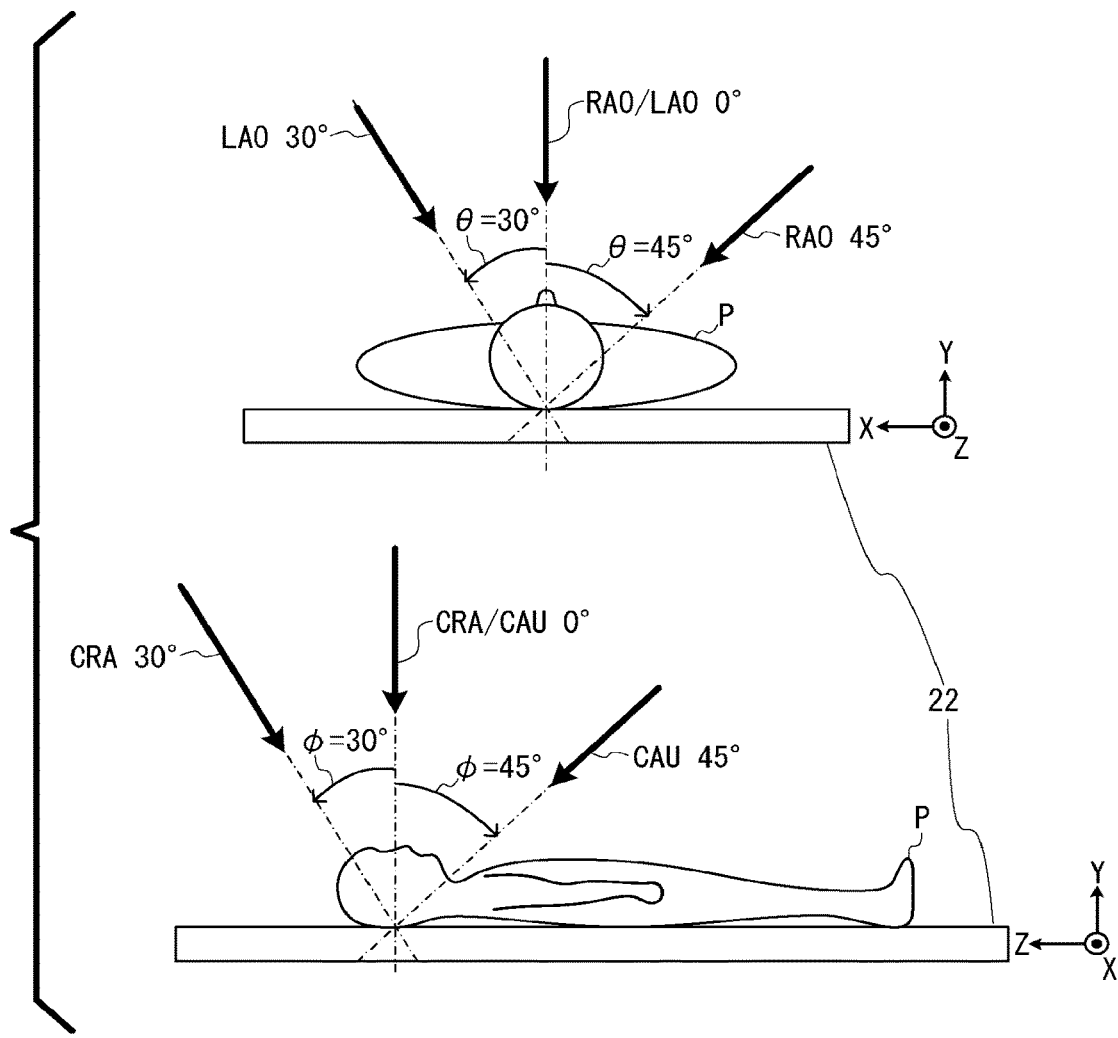
FIG. 3 is a schematic diagram showing an example of a definition of an X-ray irradiation direction.

FIG. 3 is a schematic diagram showing an example of a definition of an X-ray irradiation direction. As an example here, the object P is assumed to be loaded on the table 22 in a face-up position in such a manner that its body axis matches the Z axis direction of the apparatus coordinate system. The upper part of FIG. 3 is a schematic diagram showing X-ray irradiation directions on an X-Y plane of the apparatus coordinate system. The lower part of FIG. 3 is a schematic diagram showing X-ray irradiation directions on a Y-Z plane of the apparatus coordinate system.

An X-ray irradiation direction is defined by the first angle $\theta$ and the second angle $\varphi$. The first angle $\theta$ is an angle from the Y axis direction on an X-Y plane of the apparatus coordinate system (i.e., the vertical direction) shown in the upper part of FIG. 3, for example. The second angle $\varphi$ is an angle from the Y axis direction on a Y-Z plane of the apparatus coordinate system shown in the lower part of FIG. 3, for example.

As shown in the upper part of FIG. 3, when an X-ray irradiation direction is tilted from the Y axis direction as the reference direction toward the RAO (Right anterior oblique) direction of the object P by $\theta°$ on an X-Y plane, the first angle θ is expressed as RAO θ°. In the upper part of FIG. 3, an example of RAO 45° which is tilted toward the RAO direction by 45° is shown.

In addition, when an X-ray irradiation direction is tilted from the Y axis direction as the reference direction toward the LAO (left anterior oblique) direction of the object P by θ° on an X-Y plane as shown in the upper part of FIG. 3, the first angle θ is expressed as LAO θ°. In the upper part of FIG. 3, an example of LAO 30° which is tilted toward the LAO direction by 30° is shown. When an X-ray irradiation direction matches the Y axis direction as the reference direction on an X-Y plane, the first angle θ is expressed as RAO/LAO 0°.

As shown in the lower part of FIG. 3, when an X-ray irradiation direction is tilted from the Y axis direction as the reference direction toward the CRA (cranial) direction of the object P by φ° on a Y-Z plane, the second angle φ is expressed as CRA φ°. In the lower part of FIG. 3, an example of CRA 30° which is tilted toward the CRA direction by 30° is shown.

In addition, when an X-ray irradiation direction is tilted from the Y axis direction as the reference direction toward the CAU (caudal) direction of the object P by φ° on a Y-Z plane as shown in the lower part of FIG. 3, the second angle φ is expressed as CAU φ°. In the lower part of FIG. 3, an example of CAU 45° which is tilted toward the CAU direction by 45° is shown. When an X-ray irradiation direction matches the Y axis direction as the reference direction on a Y-Z plane, the second angle p is expressed as CRA/CAU 0°.

In general, many images are obtained as frontal images (RAO/LAO 0°) or side images (RAO 90° or LAO 90°), and such images are used for observing the dynamic state as a whole. However, an appropriate angle for observation is different for each blood vessel and each disease, and information on an X-ray irradiation direction recorded based on the C-arm moving structure 32 (e.g., RAO 30°) is added to each X-ray image as accompanying information, for example.

As to frontal images and side images (i.e., images whose first angle θ is 0° or 90°, and whose second angle φ is 0° or 90°), doctors are accustomed to observing such images and it is considered that doctors can easily judge from which angle the image is obtained by observing it. In other words, it is considered that such X-ray irradiation directions are unlikely to become feature information items.

On the other hand, when at least one of the first angle θ and the second angle φ is not 0° or 90°, it is probably difficult for a doctor to judge from which direction the image is imaged unless the doctor refers to accompanying information and the like for the X-ray irradiation direction at the time of imaging. In other words, it is considered that such X-ray irradiation directions are likely to become feature information items.

For the above reason, the alternate control function 46a is assumed to refer to the X-ray irradiation direction recorded in accompanying information of an image file and to determine the X-ray irradiation direction as a comment alternate when at least one of the first angle θ and the second angle φ is not 0° or 90°, as an example here.

However, this is only an example. As another example, the alternate control function 46a may determine the X-ray irradiation direction as a comment alternate when at least one of the first angle θ and the second angle φ is not 0°, 45°, or 90°. In other words, when the X-ray irradiation direction is different from the directions which are frequently used, the alternate control function 46a may determine this X-ray irradiation direction as a comment alternate. Additionally or alternatively, the alternate control function 46a may always determine the X-ray irradiation direction as a comment alternate. In addition, when at least one of the first angle θ and the second angle φ is not 0° or 90°, the alternate control function 46a may assign higher priority as a comment alternate to the X-ray irradiation direction.

The alternate control function 46a determines remaining comment alternates except the comment alternates determined in the methods like the first to fourth examples so that the number of comment alternates becomes the appropriate number (e.g., approximately ten to twenty). As to determination of remaining comment alternates, the accompanying information of the target X-ray image is significant. In accompanying information of an image file, for example, the following information items on examination and/or treatment is included.

Firstly, at least five information items such as a full name, gender, age, height, and weight of the object P each of which can become comment alternates are included as object information.

Secondly, information items of an imaging part such as a head and a chest are included.

Thirdly, at least seven information items such as posture of the object P on the table 22, an imaging region defined by the apparatus coordinate system, a tube current, a tube voltage, X-ray pulse width, X-ray dose, an X-ray irradiation direction each of which can become comment alternates are included as X-ray imaging conditions.

Fourthly, an information item of a blood vessel to be imaged is included.

Fifthly, an information item of a disease name is included.

Sixthly, information on a treatment stage is included.

Seventhly, when a medical device is used, (a) an information item of a used medical device such as a catheter, a stent, and a clot removal device and/or (b) a distinguishing name of a medical treatment relevant to a medical device are included.

Eighthly, when medical agent is used, an information item of used medical agent is included.

Although information items other than the above-described information items are included in the information items on examination and/or treatment, the alternate control function 46a selects feature information items by which the target X-ray image is easily distinguished from other X-ray images, from the above information items on examination and/or treatment. The alternate control function 46a can extract different points in information items on examination and/or treatment between the target object image and other images each of which depicts the same object and was imaged at an imaging time being separate from the imaging time of the target image, by referring to text data of voice detected by the voice recognizer 49 during examination or treatment as an example. The alternate control function 46a can select one or plural comment alternates from those information items on examination and/or treatment extracted in the above manner.

If all the keywords which may possibly become comment alternates are picked up from the character data generated by the voice recognizer 49, risk of including many keywords with low relevance to the target object image is high. Thus, for example, the alternate control function 46a selects keywords each of which matches one of the keywords recognized by the voice recognizer 49, from a group of keywords registered in database of the memory circuitry 44 of the X-ray diagnostic apparatus 10, and determines the selected keywords as comment alternates. The above-described keyword group may be generated so as to include all the information items on examination and/or treatment of files of all the object images having been already generated by the X-ray diagnostic apparatus 10, for example.

However, a new medical device or new medical agent is sometimes used. It is an operational burden for a user to register information on a new medical device and/or new medical agent such as its name and its medical use each time a new medical device and/or new medical agent is used. For the above reason, the alternate control function 46a selects each keyword which does not exist in the database of the memory circuitry 44, from the keywords recognized by the voice recognizer 49, and records each selected keyword in the memory circuitry 44 in association with its detection time and date.

Moreover, the alternate control function 46a calculates appearance frequency of each keyword which is recognized by the voice recognizer 49 but does not exist in the database, and stores the appearance frequency in the memory circuitry 44. Thereby, the alternate control function 46a updates the database by adding a keyword whose appearance frequency reaches a predetermined value. In addition, the alternate control function 46a may assign higher priority to keywords recognized by the voice recognizer 49 than priority of the keyword group registered in the memory circuitry 44.

Incidentally, though the hardware configuration of the X-ray diagnostic apparatus 10 has been explained as a single-plane type including only one imaging system, this is only an example. The X-ray diagnostic apparatus 10 may be configured as a biplane type including two imaging systems as a frontal system and a lateral system each of which includes the X-ray tube 34, the collimator 35 and the X-ray detector 36. As an example here, when the X-ray diagnostic apparatus 10 is configured as a biplane type, the alternate control function 46a may determine an information item indicating from which of the frontal system and the lateral system an image is obtained as a comment alternate.

In addition, a flow of an operation in which appropriate number of comment alternates are determined by the second processing circuitry 46 as feature information items of each DSA image will be explained by reference to FIG. 7 described below. However, methods of determining appropriate number of comment alternates in the case of other object images such as a non-contrast X-ray image are similar to the above-described methods.

In the case of a non-contrast X-ray image except a mask image for generating DSA images, there is a high possibility that the non-contrast X-ray image is generated in examination focusing on elements excluding blood vessels such as bone fracture, disc herniation, and pneumothorax. Accordingly, in the case of a non-contrast X-ray image, the alternate control function 46a may exclude names of blood vessels from comment alternates. As an example here, the alternate control function 46a is assumed to include a name of a bone in comment alternates in the case of a non-contrast X-ray image, regardless of an imaging part. Moreover, the alternate control function 46a may include a name of an internal organ in comment alternates in addition to a name of a bone, in the case of a non-contrast truncal X-ray image.

When a bone name and an organ name is included in the accompanying information of the target X-ray image, the alternate control function 46a may determine the bone name and the organ name as comment alternates. When neither a bone name nor an organ name is included in the accompanying information of the target X-ray image, the image analysis function 46b identifies a name of a bone depicted in the target X-ray image, and also identifies a name of an internal organ depicted in the target X-ray image organ if possible.

Thus, data of the bony framework and bony shape of a standard human body are preliminarily stored in the memory circuitry 44 for each bone name. Further, data of position and shape of internal organs of a standard human body are also preliminarily stored in the memory circuitry 44 for each organ name. The above-described "preliminarily" means a concept similar to that of the data of a blood vessel model.

The image analysis function 46b acquires an imaging part included in the accompanying information of the file of the target X-ray image. Then, the image analysis function 46b acquires data corresponding to the acquired imaging part out of (a) the above-described data of the bony framework and bony shape of a standard human body or (b) the above-described data of position and shape of internal organs of a standard human body, from the memory circuitry 44.

The image analysis function 46b identifies the name of the bone and the name of the internal organ depicted in the target X-ray image by performing known pattern matching processing based on the acquired data on the target X-ray image, and outputs the identified name of the bone and the internal organ to the alternate control function 46a.

Next, more concrete examples of appropriate number of comment alternates will be explained.

FIG. 4 is a schematic diagram showing an example of every choice having been already stored in the memory circuitry 44 since the start-up time of the X-ray diagnostic apparatus 10 out of all the comment alternates relevant to head imaging, when head imaging is designated in a treatment plan.

Incidentally, a keyword and the like except all the choices stored in the memory circuitry 44 may be actually displayed as comment alternates based on, for example, the keywords recognized by the voice recognizer 49 as described above.

In the example of FIG. 4, forty choices including a femoral artery, a descending aorta, an aortic arc, a left subclavian artery, a right subclavian artery, a brachiocephalic artery, a common carotid artery, a right internal carotid artery, a right anterior cerebral artery, a right middle cerebral artery, a left internal carotid artery, a left anterior cerebral artery, a left middle cerebral artery, a left vertebral artery, a right vertebral artery, a basilar artery, a right external carotid artery, a left external carotid artery, an observational angle, contrast agent, antiplatelet agent, anticoagulant agent, thrombolytic, a guidewire, a catheter, a stent for a carotid artery, an intracranial stent, a balloon, preparatory expansion, ex-post expansion, coil embolization, stent placement, a first coil, a second coil, a third coil, a dome filling coil, catheter insertion, stent-assisted coil embolization, a double catheter technique, and balloon-assisted coil embolization are preliminarily stored for head imaging.

Figure 5:
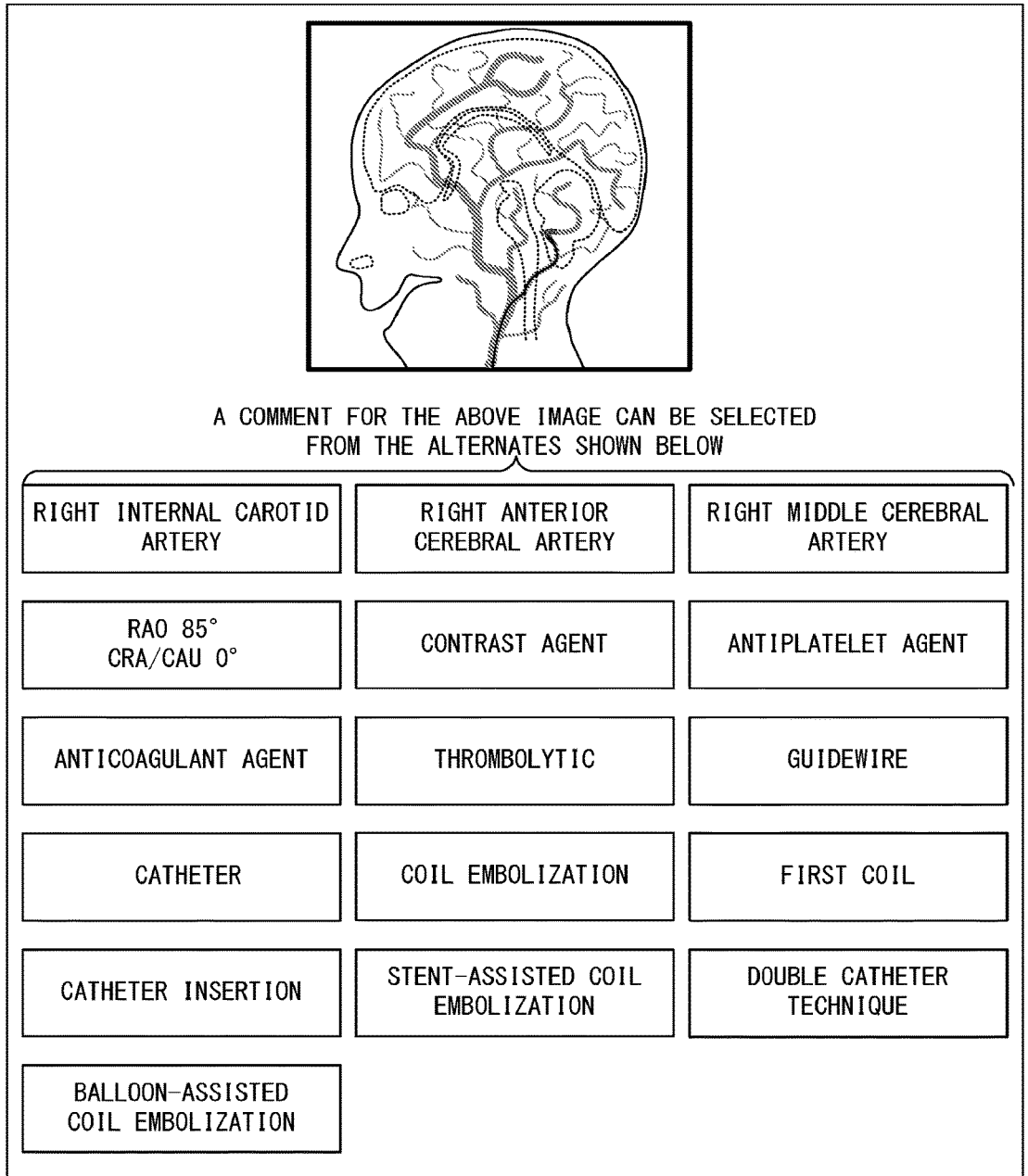
FIG. 5 is a schematic diagram showing an example of a screen of comment alternates displayed when a catheter is positioned at a right internal carotid artery in a head image of coil embolization.

If the name of the blood vessel superimposed with a catheter in the target image is a right internal carotid artery and the operative treatment relevant to this image is coil embolization, the alternate control function 46a narrow all the choices in FIG. 4 down to, e.g., sixteen choices like FIG. 5, as actually displayed comment alternates.

FIG. 5 is a schematic diagram showing an example of a screen of comment alternates displayed when a catheter is positioned at a right internal carotid artery in a head image of coil embolization. As an example in FIG. 5, sixteen comment alternates including a right internal carotid artery, a right anterior cerebral artery, a right middle cerebral artery, an observational angle, contrast agent, antiplatelet agent, anticoagulant agent, thrombolytic, a guidewire, a catheter, coil embolization, a first coil, catheter insertion, stent-assisted coil embolization, a double catheter technique, and balloon-assisted coil embolization are displayed.

As to the observational angle in FIG. 5, a concrete value at the imaging time of the target object image such as RAO 85° and CRA/CAU 0° is displayed. In addition, since the second coil, the third coil, and the dome-filling coil cannot be inserted before insertion of the first coil due to limitations of a treatment procedure, the alternate control function 46a excludes these coils from all the choices in FIG. 4.

Figure 6:
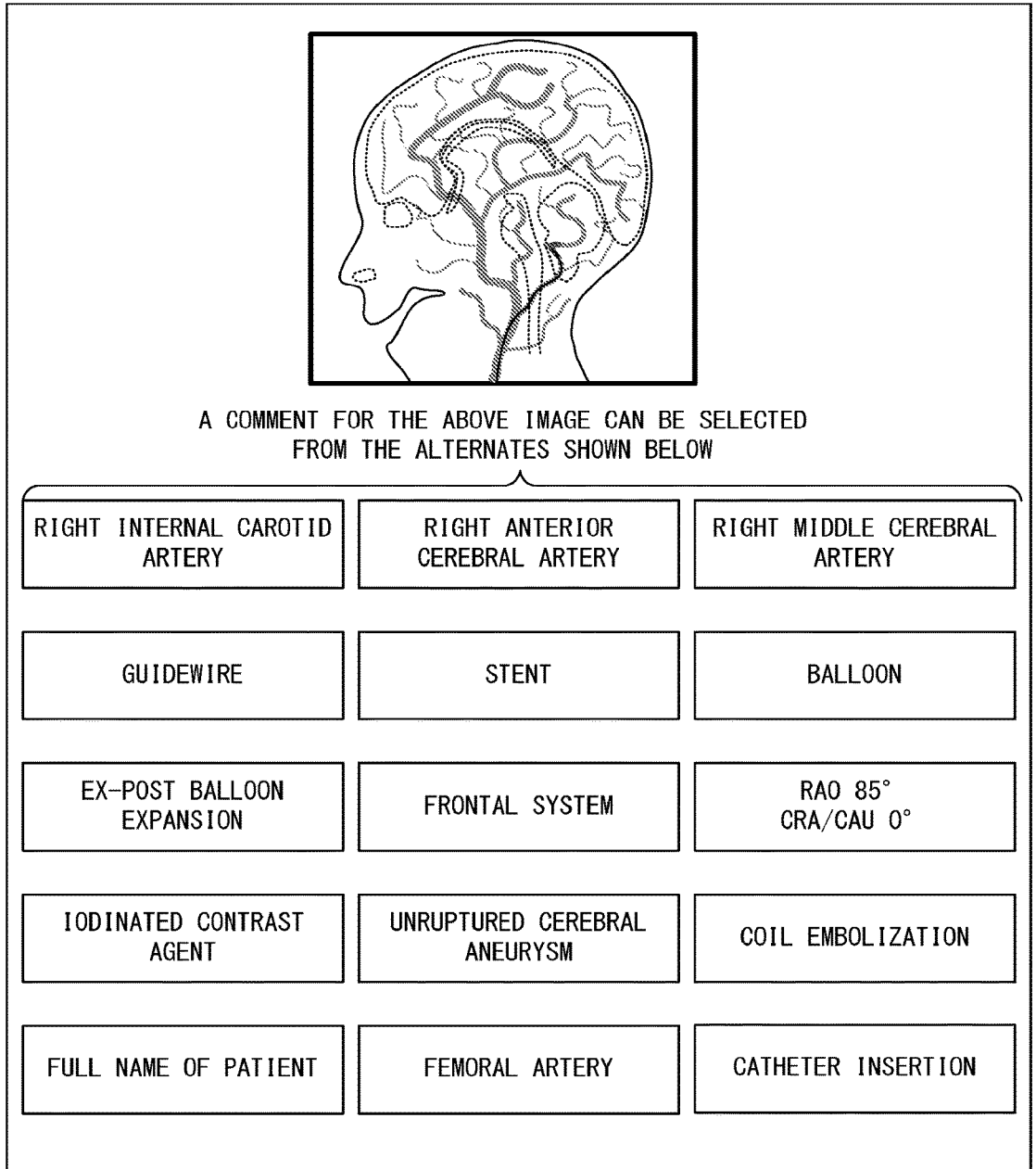
FIG. 6 is a schematic diagram showing another example of a screen in which appropriate number of comment alternates with respect to an object image determined by a alternate control function are displayed.

FIG. 6 is a schematic diagram showing another example of a screen on which appropriate number of comment alternates with respect to an object image determined by the alternate control function 46a are displayed. Although a case of a DSA image for a head is considered as an object image as an example here, appropriate number of comment alternates is displayed also in the case of another object image such as a non-contrast X-ray image.

In the example of FIG. 6, a magnified view of the object image is displayed on the upper side of the screen of the display 47 and, for example, fifteen comment alternates for this object image are displayed on the lower side of the screen. Since the example of FIG. 6 shows a DSA image of the object P diagnosed as an unruptured cerebral aneurysm imaged at the time of coil embolization as an example here, "unruptured cerebral aneurysm" as a disease name and "coil embolization" as a treatment name are displayed as comment alternates.

Since "insert a catheter from the femoral artery" is detected as a keyword during imaging and treatment by the voice recognizer 49, "femoral artery" and "catheter insertion" as subordinate concepts of the treatment name are displayed as comment alternates.

In addition, since "RAO 85° CRA/CAU 0°" is not a direction frequently used as an X-ray irradiation direction, it is displayed as a comment alternate.

Since the treatment stage at the time of imaging the target image has been identified as ex-post balloon expansion, ex-post balloon expansion is displayed as a comment alternate.

Moreover, "right internal carotid artery" identified as a name of a blood vessel by the above-described pattern matching with a CT image is displayed as a comment alternate together with "right anterior cerebral artery" and "right middle cerebral artery" in the downstream of this right internal carotid artery.

Since the target image is an X-ray image imaged by the frontal system of a biplane type, "frontal system" is displayed as a comment alternate.

Furthermore, "guidewire", "catheter", and "stent" as medical device used during imaging are displayed comment alternates.

Although the above-described comment alternates and its number are only examples for concretizing the explanation, a user can select a comment for the target object image from the displayed comment alternates via the input device 48. In addition, the alternate control function 46a may change display order of the appropriate number of comment alternates based on priority of each of these comment alternates from all the choices comment alternates, so that these comment alternates are displayed on the display 47 in the order of higher priority. Thereby, a user can select a comment alternate with higher priority via the input device 48.

<Operation of Present Embodiment>

Figure 7:
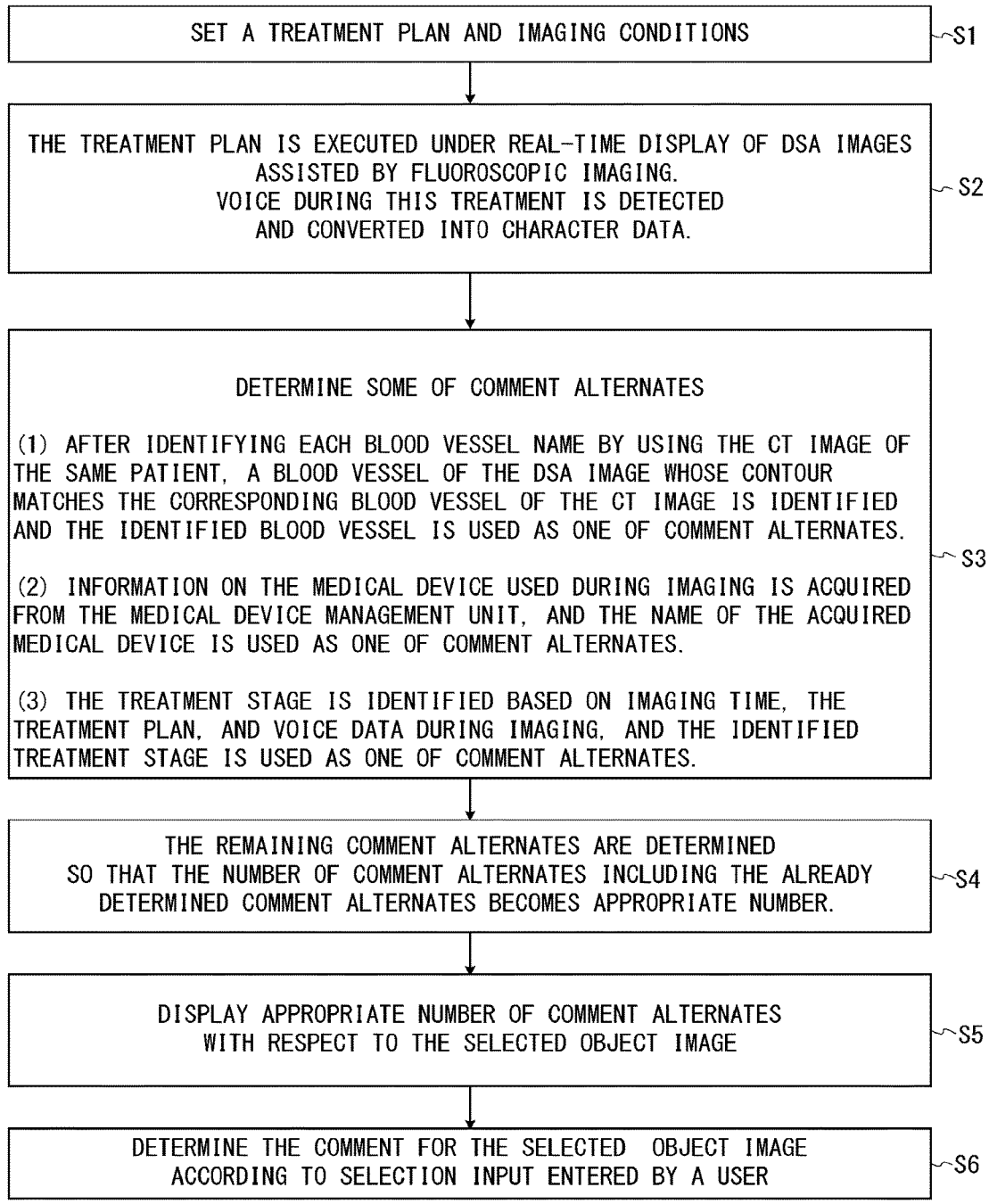
FIG. 7 is a flowchart showing an example of an operation performed by the X-ray diagnostic apparatus of the present embodiment.

FIG. 7 is a flowchart showing an example of an operation performed by the X-ray diagnostic apparatus 10 of the present embodiment. As an example here, a case where a treatment plan under fluoroscopic imaging is determined and then the treatment plan is executed while sequentially imaging time-sequential X-ray images of the same imaging region of the same object before and after injection of contrast agent will be explained.

Hereinafter, according to the step numbers in the flowchart shown in FIG. 7, an operation performed by the X-ray diagnostic apparatus 10 will be explained by referring to the above-described FIG. 1 to FIG. 6 as required.

First, the first processing circuitry 42 reads out the respective programs from the memory circuitry 44 so as to implement the system control function 42a, the X-ray data generation function 42b, and the DSA image generation function 42c. In addition, the second processing circuitry 46 reads out the respective programs from the memory circuitry 44 so as to implement the alternate control function 46a, the image analysis function 46b, and the image processing function 46c.

[Step S1] The system control unit 42a (FIG. 1) sets a treatment plan and imaging conditions, based on some conditions inputted via the input device 48.

Afterward, the processing proceeds to the Step S2.

[Step S2] Before and after injection of contrast agent, the X-ray data generation function 42b generates projection data of time-sequential X-ray images on the same region of the same object P under a conventionally known imaging operation.

Specifically, before injection of contrast agent, the high-voltage generator 31 supplies the X-ray tube 34 with high voltage under the control of the system control function 42a, the X-ray tube 34 generates X-rays, and the irradiation region of X-rays on the object P is controlled by the collimator 35.

The X-ray detector 36 converts X-rays having passed through the object P into electric signals, and outputs the electric signals to the X-ray data generation function 42b.

The X-ray data generation function 42b generates projection data of an X-ray image (i.e., a mask image) from the inputted electric signals. The projection data generation unit 42b outputs the generated projection data to the DSA image generation function 42c and stores the generated projection data in the memory circuitry 44.

Afterward, while positions of the table 22 and the C-arm 33 are fixed, contrast agent is injected to the object P by remote control of a non-illustrated contrast agent injection apparatus and then X-ray images (i.e., contrast images) for the same imaging region as the mask image are imaged at plural timings in a similar manner as described above. Afterward, projection data of the contrast images are inputted to the DSA image generation function 42c and stored in the memory circuitry 44.

The DSA image generation function 42c generates image data of time-sequential DSA images of multiple time phases based on the projection data of the mask image and the contrast images, and causes the display 47 to sequentially display these DSA images on a real-time basis.

Under the fluoroscopic imaging, a guidewire operation device 200 is used as an example and the treatment plan is executed. The medical device management unit 43 updates and records information on medical devices used in the treatment on a real-time basis, in the above-described manner. In addition, the voice recognizer 49 detects and records voice during examination or treatment, and converts the recorded voice into text data. Moreover, the DSA image generation function 42c stores files of sequentially generated image data of DSA images in the memory circuitry 44.

Afterward, the processing proceeds to the Step S3.

[Step S3] During or after procedures, thumbnail images of a large number of DSA images are collectively displayed on the display 47, for example. A user selects an object image by selecting one arbitrary thumbnail image or designating a specific image via the input device 48, for example. Although the alternate control function 46*a* finally narrows comment alternates for the selected object image (i.e., DSA image in this example) down to appropriate number, the alternate control function 46*a* determines some of the appropriate number of the comment alternates in this step S3.

First, the alternate control function 46*a* acquires the information items on examination and/or treatment included in the accompanying information of the selected object image (i.e., the target object image). Next, as an example here, it is assumed that volume data of the same object P generated by an X-ray CT apparatus exist. In this case, the image analysis function 46*b* identifies the name of each blood vessel extracted from the volume data acquired via the communication device 41 and generates two-dimensional projection data from the volume data so that the projection direction of the selected object image matches the projection direction of the projection data to be generated, as explained in FIG. 2. The image analysis function 46*b* outputs the name of each blood vessel of the selected object image whose contour matches the corresponding blood vessel depicted in the two-dimensionally projected CT image, to the alternate control function 46*a*.

The alternate control function 46*a* determines the name of each blood vessel inputted from the image analysis function 46*b* as a comment alternate, and determines the name of each blood vessel in the downstream of each inputted blood vessel as a comment alternate if it exists.

Although the alternate control function 46*a* includes the name of each blood vessel in the downstream in the comment alternates if it exists, this method is only an example of determining comment alternates. In other word, as to blood vessels in the downstream of each blood vessel inputted to the alternate control function 46*a* from the image analysis function 46*b*, they may be excluded from the comment alternates.

In addition, if a blood vessel with high priority in the downstream of the blood vessel inputted to the alternate control function 46*a* exists, the alternate control function 46*a* may cause the display 47 to preferentially display such a blood vessel, for example. In this case, the alternate control function 46*a* changes the display order of the comment alternates based on the priority assigned to each blood vessel.

Further, the alternate control function 46*a* determines the name of the medical device used at the imaging time of the selected object image as a comment alternate, by accessing the medical device management unit 43 as mentioned above. When an embolization coil is used, the alternate control function 46*a* determines calculated VER as a comment alternate as mentioned above.

Moreover, the alternate control function 46*a* acquires information on the treatment plan determined in the step S1 by accessing the system control function 42*a*, and determines the treatment stage at the imaging time of the selected object image based on the information on the treatment plan in the above-described manner, for example. The alternate control function 46*a* determines the treatment stage at the imaging time of the selected object image as a comment alternate.

Furthermore, the alternate control function 46*a* refers to the file of the image data of the selected object image so as to acquire the X-ray irradiation direction. When the X-ray irradiation direction of the selected object image is different from any of the frequently-used directions as described above, the alternate control function 46*a* determines this X-ray irradiation direction as a comment alternate as an example here.

Afterward, the processing proceeds to the Step S4.

[Step S4] The alternate control function 46*a* determines the remaining comment alternates except the comment alternate determined in the step S3, based on the information items on examination and/or treatment of the selected object image. The remaining comment alternates are determined in such a manner that the number of comment alternates including the comment alternates determined in the step S3 becomes the appropriate number. As to this determination method, it has already been explained.

Afterward, the processing proceeds to the Step S5.

[Step S5] The alternate control function 46*a* causes the display 47 to display the appropriate number of comment alternates determined in the steps S3 and S4 (see FIG. 4).

Afterward, the processing proceeds to the Step S6.

[Step S6] The input device 48 includes the comment alternate selected by a user's operation in the accompanying information of the data file of the target object image as the comment of the target object image. Additionally or alternatively, the input device 48 inserts characters indicative of the comment alternate selected by a user's operation (i.e., a keyword indicative of the feature information) into an image region avoiding the target region of the target object image. Incidentally, the input device 48 may overwrite the comment alternate selected by a user as a choice which is inserted into the target object image at the time of saving as information for making it more understandable.

As an example in the present embodiment, when it is determined that a coil is used as a medical device in the step S3, information on the inserted coil such as its name, its diameter and its length is added as character information to a partial region of the target object image by the alternate control function 46*a* or the input device 48 as mentioned above. When VER is obtained, the above-described coil information is added together with VER.

In addition, when a generic term is displayed as a comment alternate and this generic term is selected by a user, not only this generic term but also information concretizing this generic term are added to the image file.

Specifically, consider a case where the alternate control function 46*a* causes the display 47 to display a generic term (i.e., collective term of the same type of medical device) "coil" as one of comment alternates and "coil" is selected by a user from these comment alternates. In this case, the input device 48 adds combined information of the concrete name of the coil used at the time of imaging the target image (for which comment is selected) and its associated information such as the diameter and length to the image file of this target image. At the same time, the display 47 displays all of the combined information.

Incidentally, the alternate control function 46*a* may assign priority to each medical device such as coils and a stent for a carotid artery and cause the display 47 to preferentially display them as comment alternates, for example. In this case, the alternate control function 46*a* changes the display order of the comment alternates so that they are displayed in the order of higher priority.

As another example, consider a case where the alternate control function 46*a* causes the display 47 to display the collective term "contrast agent" as one of plural comment alternate and "contrast agent" is selected by a user from those comment alternates. In this case, the input device 48 adds combined information of "contrast agent" as the collective term of medical agent and the concrete name of the contrast agent (e.g., water-soluble iodine contrast agent) used at the time of imaging the target image (for which comment is selected) to the image file of this target image. At the same time, the display 47 displays all of the combined information.

As still another example, consider a case where the alternate control function 46*a* causes the display 47 to display an index name "VER" as one of plural comment alternates and "VER" is selected by a user from these comment alternates. In this case, the input device 48 adds combined information of "VER" as an index name and the concrete VER value at the time of imaging the target image (for which comment is selected) to the image file of this target image. At the same time, the display 47 displays all of the combined information.

The foregoing is the explanation of the operation performed by the X-ray diagnostic apparatus 10 of the present embodiment.

<Effects of Present Embodiment>

According to the present embodiment, comment alternates for the target object image are narrowed down to the appropriate number by the alternate control function 46*a* and then displayed on the display 47. In addition, the alternate control function 46*a* changes the display order of the plural comment alternates, and these comment alternates are displayed on the display 47 according to the changed display order. Thus, since a user does not need to manually enter a comment or select a comment from a pile of alternates, an operational burden for a user is reduced.

In the extraction processing of narrowing comment alternates down to the appropriate number, the alternate control function 46*a* refers to not only information items on examination and/or treatment included in the accompanying information of the file of the target object image but also keywords which were detected during imaging and converted into text data by the voice recognizer 49.

Additionally, the alternate control function 46*a* refers to blood vessel information obtained from volume data of the same object P generated by another image diagnostic apparatus in the extraction processing. Moreover, the alternate control function 46*a* refers to information on a medical device used during imaging by accessing the medical device management unit 43. Accordingly, the alternate control function 46*a* can select feature information items by which the target object image is distinguished from other images, as comment alternates.

In conventional technology, information entered or selected by a user's operation matches information to be added to an image file. By contrast, in the present embodiment, when a generic term is displayed as one of comment alternates and this generic term is selected by a user, information which further concretizes the selected generic term is added to the image file and displayed. For example, when "VER" as one of comment alternates is selected, a concrete value of VER is displayed and added to the file of the target object image. Since object images are made more understandable than conventional technology by the above-described automatic processing of the X-ray diagnostic apparatus 10, operation time relevant to diagnosis and treatment may be shortened.

According to one of the above-described embodiments, as to a comment added to a certain region of a file of an X-ray image such as a comment region for making various conditions at the imaging time of the X-ray image more understandable, a burden of operating an X-ray diagnostic apparatus on a user can be reduced by supporting the operation of entering a comment.

<Supplementary Notes on Present Embodiment>

[1] An example of (a) performing pattern matching processing between a DSA image of the object P generated by the X-ray diagnostic apparatus 10 and each blood vessel extracted from volume data of the same object P generated by an X-ray CT apparatus and (b) selecting a name of a blood vessel of the DSA image whose contour matches the corresponding blood vessel of the volume data as a comment alternate has been explained in the above-described embodiment. However, embodiments of the present invention are not limited to such an aspect. As to a method of determining a name of blood vessel to be selected as one of comment alternates, for example, the following first or second modification may be used.

As the first modification, the alternate control function 46*a* searches text data generated by the voice recognizer 49 during imaging for a keyword indicating a name of blood vessel, e.g, "insert the stent in the . . . artery from now". The alternate control function 46*a* selects a blood vessel name matching the searched keyword from blood vessel names in the accompanying information of the target object image.

As the second modification, when a large number of time-sequential X-ray images are generated for the same imaging region by X-ray imaging during insertion of a medical device such as a guidewire, the image analysis function 46*b* detects blood vessel shape by tracking the trajectory of the tip of the medical device in the respective X-ray images. The image analysis function 46*b* selects the blood vessel having the closest shape to the detected blood vessel shape from the standard blood vessel models stored as data, and outputs the selected blood vessel name to the alternate control function 46*a*. The alternate control function 46*a* can determine the blood vessel name inputted from the image analysis function 46*b* as a comment alternate corresponding to those time-sequential X-ray images for the same imaging region.

[2] An example in which the medical device management unit 43 included in the X-ray diagnostic apparatus 10 updates and stores the current usage conditions of the respective medical devices and the past usage information of the respective medical devices on a real-time basis has been explained in the above-described embodiment. However, embodiments of the present invention are not limited to such an aspect.

The medical device management unit 43 may be disposed outside the X-ray diagnostic apparatus 10 as a component independent of the X-ray diagnostic apparatus 10. In this case, the medical device management unit 43 updates and stores not only the current usage conditions and the past usage information of the respective medical devices used with the X-ray diagnostic apparatus 10 but also the current usage conditions and the past usage information of the respective medical devices used with other image diagnostic apparatuses, on a real-time basis. Then, the extraction control function 46*a* may acquire information on medical devices used for at least one of examination and treatment together with the X-ray diagnostic apparatus 10 from the external medical device management unit 43 via the communication device 41, like the above-described embodiment.

[3] In the above-described embodiment, an example in which the second processing circuitry 46, the input device 48 and the voice recognizer 49 are installed in the X-ray diagnostic apparatus 10 has been explained. However, embodiments of the present invention are not limited to such an aspect. The second processing circuitry 46, the input device 48, and the voice recognizer 49 in the above-described embodiment may be installed in another image diagnostic apparatus capable of imaging bloodstream images before and after injection of contrast agent such as an X-ray CT apparatus and a magnetic resonance imaging apparatus, for example.

[4] An input support program for image feature information (i.e., a support program for inputting a comment with respect to an object image) may be generated by coding the processing from the Steps S2 to S6 in FIG. 7. The second processing circuitry 46 in FIG. 1 may be interpreted as circuitry in which such a program is installed.

Although the first processing circuitry 42 and the second processing circuitry 46 are explained as hardware in FIG. 1, in this case, the entirety of the second processing circuitry 46, the display 47, the input device 48, and the voice recognizer 49 functions as an input support system for image feature information (i.e., a comment input support system in an X-ray diagnostic apparatus).

However, the above configuration is only an example, and the first processing circuitry 42 and the second processing circuitry 46 may be configured as a first CPU (Central Processing Unit) and a second CPU, respectively. In this case, the respective components of the second CPU functions as the alternate control function 46a, the image analysis function 46b, and the image processing function 46c by the above-described support program for inputting a comment, and the entirety of the second CPU, the display 47, the input device 48, and the voice recognizer 49 functions as a support device for inputting image feature information in an X-ray diagnostic apparatus.

The above-described term "processor" means, for instance, a circuit such as a special-purpose or general-purpose CPU, an ASIC (Application Specific Integrated Circuit), a programmable logic device including an SPLD (Simple Programmable Logic Device) and a CPLD (Complex Programmable Logic Device) as examples, and an FPGA (Field Programmable Gate Array).

Although only the first processing circuitry 42 is provided as an imaging-operation control device in FIG. 1, further processing circuitry (i.e., processor) which functions as an imaging-operation control device together with the first processing circuitry 42 may be provided in the X-ray diagnostic apparatus.

Additionally, though only the second processing circuitry 46 is provided as an image processing device in FIG. 1, further processing circuitry (i.e., processor) which functions as an image processing device together with the second processing circuitry 46 may be provided in the X-ray diagnostic apparatus.

A processor implements respective functions by reading out programs stored in the memory (e.g., the memory circuitry 44) or programs directly installed in the circuit of the processor and executing the programs.

Plural memories storing programs may be provided for respective processors. Additionally or alternatively, the memory circuitry 44 in FIG. 1 may collectively store programs corresponding to all the functions of the respective processors.

[5] Correspondence between terms used in the claims and terms used in the embodiment described above will be described. Note that the correspondence described below is just some of possible interpretations for reference and should not be construed as limiting the present invention.

The information on examination and/or treatment is an example of the medical information described in the claims.

[6] While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An X-ray diagnostic apparatus which generates an object image by detecting X-rays having passed through an object, the X-ray diagnostic apparatus comprising:
a display configured to display the object image;
memory circuitry to store feature information items for distinguishing the object image from other images:
processing circuitry configured to perform display-order change processing, which is processing of changing a display order of the feature information items, and to cause the display to display the feature information items subjected to the display-order change processing as alternates; and
an input circuit configured to receive input of selecting a feature information item from the feature information items displayed on the display,
wherein the processing circuitry is further configured to
perform extraction processing which is processing of narrowing number of the feature information items down to predetermined number based on medical information related to at least one of examination and treatment,
cause the display to display the predetermined number of the feature information items extracted by the extraction processing as the alternates, and
acquire information on a treatment plan with respect to the object as the medical information and to select a treatment stage identified based on the information on a treatment plan as one of the alternates.

2. The X-ray diagnostic apparatus according to claim 1, wherein the processing circuitry is further configured to perform the display-order change processing based on priority separately assigned to the feature information items.

3. The X-ray diagnostic apparatus according to claim 1, wherein the processing circuitry is further configured to add the feature information item selected by the input received by the input circuit to a file of the object image.

4. The X-ray diagnostic apparatus according to claim 1, wherein the processing circuitry is further configured to acquire at least one of an irradiation condition of X-rays, information on the object, an imaging part, a name of an imaged blood vessel, a name of disease, a name of used medical agent, a name of a used medical device, and a name of distinguishing treatment relevant to a used device, as the medical information.

5. The X-ray diagnostic apparatus according to claim 1, wherein the processing circuitry is further configured to acquire information on a medical device used at an imaging time of the object image and volume information of an arterial aneurysm in the object image, and select VER (Volume Embolization Ratio) calculated from the information on a medical device used at an imaging time of the object image and the volume information of an arterial aneurysm in the object image, as one of alternates.

6. The X-ray diagnostic apparatus according to claim 1, wherein the processing circuitry is further configured to
cause the display to display a collective term of a medical device as one of the alternates, and
add information by which a medical device used at an imaging time of the object image is identified to a file of the object image, when the input circuit receives input of selecting the collective term of a medical device.

7. The X-ray diagnostic apparatus according to claim 1, wherein the processing circuitry is further configured to
cause the display to display a collective term of medical agent as one of the alternates, and
add information by which medical agent used at an imaging time of the object image is identified to a file of the object image, when the input circuit receives input of selecting the collective term of medical agent.

8. The X-ray diagnostic apparatus according to claim 1, wherein the processing circuitry is further configured to
cause the display to display an index name as one of the alternates, and
add combined information of an index value of the object image and the index name to a file of the object image, when the input circuit receives input of selecting the index name.

9. The X-ray diagnostic apparatus according to claim 1, further comprising a voice recognizer configured to detect voice around the object and convert detected voice into text data, and
wherein the processing circuitry is further configured to select a blood vessel name extracted by the extraction processing which matches a blood vessel name converted into text data by the voice recognizer, as one of the alternates.

10. An X-ray diagnostic apparatus which generates an object image by detecting X-rays having passed through an object, the X-ray diagnostic apparatus comprising:
a display configured to display the object image:
memory circuitry to store feature information items for distinguishing the object image from other images;
processing circuitry configured to perform display-order change processing, which is processing of changing a display order of the feature information items, and to cause the display to display the feature information items subjected to the display-order change processing as alternates: and
an input circuit configured to receive input of selecting a feature information item from the feature information items displayed on the display,
wherein the processing circuitry is further configured to acquire information on a medical device used at an imaging time of the object image, and
select a treatment stage at the imaging time estimated from the medical device used at the imaging time as one of the alternates.

11. The X-ray diagnostic apparatus according to claim 10, wherein the processing circuitry is further configured to
perform extraction processing which is processing of narrowing number of the feature information items down to predetermined number based on medical information related to at least one of examination and treatment, and
cause the display to display the predetermined number of the feature information items extracted by the extraction processing as the alternates.

12. The X-ray diagnostic apparatus of claim 10, wherein the processing circuitry is further configured to perform the display-order change processing based on priority separately assigned to the feature information items.

13. The X-ray diagnostic apparatus according to claim 10, wherein the processing circuitry is further configured to add the feature information item selected by the input received by the input circuit to a file of the object image.

14. The X-ray diagnostic apparatus according to claim 10, wherein the processing circuitry is further configured to
cause the display to display a collective term of a medical device as one of the alternates, and
add information by which a medical device used at an imaging time of the object image is identified to a file of the object image, when the input circuit receives input of selecting the collective term of a medical device.

15. The X-ray diagnostic apparatus according to claim 10, wherein the processing circuitry is further configured to
cause the display to display a collective term of medical agent as one of the alternates, and
add information by which medical agent used at an imaging time of the object image is identified to a file of the object image, when the input circuit receives input of selecting the collective term of medical agent.

16. The X-ray diagnostic apparatus according to claim 10, wherein the processing circuitry is further configured to
cause the display to display an index name as one of the alternates, and
add combined information of an index value of the object image and the index name to a file of the object image, when the input circuit receives input of selecting the index name.

17. The X-ray diagnostic apparatus according to claim 10, further comprising a voice recognizer configured to detect voice around the object and convert detected voice into text data,
wherein the processing circuitry is further configured to select a blood vessel name extracted by the extraction processing which matches a blood vessel name converted into text data by the voice recognizer, as one of the alternates.

18. The X-ray diagnostic apparatus according to claim 10, wherein the processing circuitry is further configured to
acquire information on a medical device used at an imaging time of the object image and volume information of an arterial aneurysm in the object image, and
select VER (Volume Embolization Ratio) calculated from the information on a medical device used at an imaging time of the object image and the volume information of an arterial aneurysm in the object image, as one of alternates.

19. An X-ray diagnostic apparatus which generates an object image by detecting X-rays having passed through an object, the X-ray diagnostic apparatus comprising:
a display configured to display the object image;
memory circuitry to store feature information items for distinguishing the object image from other images;
processing circuitry configured to perform display-order change processing, which is processing of changing a display order of the feature information items, and to cause the display to display the feature information items subjected to the display-order change processing as alternates; and an input circuit configured to receive input of selecting a feature information item from the feature information items displayed on the display, wherein the processing circuitry is further configured to acquire volume data of a same object which are generated after injection of contrast agent to the same object by an X-ray CT apparatus, extract contours of respective blood vessels from the volume data, identify names of the respective blood vessels extracted from the volume data, based on pattern matching between the contours of respective blood vessels extracted from the volume data and contours stored as data for respective blood vessels, select a blood vessel matching a blood vessel extracted from the object image in terms of contour from the respective blood vessels whose names are identified, by performing pattern matching processing, and select a name of the blood vessel selected by the pattern matching processing, as one of the alternates.

20. The X-ray diagnostic apparatus according to claim 19, wherein the processing circuitry is further configured to select the name of the blood vessel selected by the pattern matching processing, as one of the alternates, and select a name of a blood vessel in downstream of the blood vessel selected by the pattern matching processing, as one of the alternates.

* * * * *